(12) United States Patent
Chien et al.

(10) Patent No.: US 10,596,963 B2
(45) Date of Patent: Mar. 24, 2020

(54) FATIGUE ALARM APPARATUS AND METHOD

(71) Applicant: LATTICE ENERGY TECHNOLOGY CORPORATION, New Taipei (TW)

(72) Inventors: Ta-Yi Chien, Taichung (TW); Pai-Hsiang Cheng, Taipei (TW); Ying-Ju Lai, Taichung (TW); Chang-Sheng Lin, Taichung (TW); Yung-Chou Chen, Taipei (TW); Guan-Hua Chen, Taipei (TW); Hsiang-Fu Fan, New Taipei (TW); Yu-Kai Lin, Taipei (TW); Wen-Jing Xie, New Taipei (TW)

(73) Assignee: LATTICE ENERGY TECHNOLOGY CORPORATION (TW)

( * ) Notice: Subject to any disclaimer, the term of this patent is extended or adjusted under 35 U.S.C. 154(b) by 0 days.

(21) Appl. No.: 16/170,517

(22) Filed: Oct. 25, 2018

(65) Prior Publication Data

US 2019/0126820 A1   May 2, 2019

(30) Foreign Application Priority Data

Oct. 26, 2017   (TW) .............................. 106215800 U

(51) Int. Cl.
*B60Q 9/00* (2006.01)
*G08B 21/06* (2006.01)
*B60Q 3/70* (2017.01)

(52) U.S. Cl.
CPC ................ *B60Q 9/00* (2013.01); *B60Q 3/70* (2017.02); *G08B 21/06* (2013.01)

(58) Field of Classification Search
CPC ............. B60Q 3/70; B60Q 9/00; G08B 21/06
See application file for complete search history.

(56) References Cited

U.S. PATENT DOCUMENTS

| 5,311,877 | A | * | 5/1994 | Kishi | ...................... G08B 21/06 340/575 |
| 5,682,144 | A | * | 10/1997 | Mannik | .................. G08B 21/06 257/221 |
| 5,684,455 | A | * | 11/1997 | Williams | ............... B60R 16/037 180/272 |
| 5,714,925 | A | * | 2/1998 | Lee | ......................... G08B 21/06 180/272 |
| 5,786,765 | A | * | 7/1998 | Kumakura | ............. G08B 21/06 340/576 |

(Continued)

*Primary Examiner* — Sisay Yacob
(74) *Attorney, Agent, or Firm* — Schmeiser, Olsen & Watts, LLP

(57) ABSTRACT

A fatigue alarm apparatus having a fatigue detector, a control unit and a stimulus alarm generator is illustrated. The fatigue detector detects whether a driver is drowsy. The control unit is electrically connected to the fatigue detector and the stimulus alarm generator. When the fatigue detector detects that the driver is drowsy, the stimulus alarm generator controlled by the control unit to generate two stimulus alarms having a rest time period therebetween, and then, after an interval period elapses, the control unit determines whether an alarming procedure of generating the two stimulus alarms is to be interrupted or repeated, wherein the rest time period is less than the interval period.

6 Claims, 6 Drawing Sheets

(56) References Cited

U.S. PATENT DOCUMENTS

| | | | |
|---|---|---|---|
| 6,946,965 B2 * | 9/2005 | Young | G08B 21/06 340/439 |
| 7,936,283 B2 * | 5/2011 | Kim | B62D 15/027 180/167 |
| 7,982,618 B2 * | 7/2011 | Omi | G08B 21/06 340/573.1 |
| 2013/0159041 A1 * | 6/2013 | Jayaraman | A61B 5/18 705/7.15 |

* cited by examiner

FATIGUE ALARM APPARATUS AND METHOD

CROSS-REFERENCE TO RELATED APPLICATION

This non-provisional application claims priority under 35 U.S.C. § 119(a) on Patent Application No(s). 106215800 filed in Taiwan, R.O.C. on Oct. 26, 2017, the entire contents of which are hereby incorporated by reference.

TECHNICAL FIELD

The present disclosure relates to a fatigue alarm apparatus and a fatigue alarm method, and in particular to the fatigue alarm apparatus and the fatigue alarm method, which keep drivers conscious and alert by having illusions based on pre-stimulus alpha oscillations.

RELATED ART

Drowsy driving is a factor in almost 10% of car accidents. To reduce this factor, fatigue alarm apparatuses or methods, which keep drivers conscious and alert, are commercially available.

A conventional fatigue alarm apparatus or method utilizes an infrared camera to capture images of a driver's eyes with infrared light, determines pupil locations and pupil sizes according to reflection coefficient difference between pupils and scleras, and decides whether the driver is losing his or her consciousness in the case of undetected pupils within a certain time period.

Another conventional fatigue alarm apparatus or method discerns eyelids according to features of eyebrows and a nostril and detects eyelid closing action based on change of the eyelid region. To enhance fatigue detection accuracy despite varying features of human face and generate a delayed alarm within a limited reaction time period, a long calculation time period is required.

Besides monitoring the eye's closing, another conventional fatigue alarm apparatus or method further measures the driver's breath and confirms a drowsy driving when the eyelids of the driver close for a while and the breath amount decreases too. Other biosignals, such as heart rate, blood pressure, autonomic nervous system activity and blood oxygen level, could be monitored at the same time to increase the accuracy of fatigue alarm.

In order not to miss or delay any possible alarm during drowsy driving, low thresholds of the above fatigue detection are required. As a result, frequent sound, beeps, vibration or flash for alarms become annoyances during defensive driving and further merge into the background noise due to the overloaded sensory.

SUMMARY

An objective of the present disclosure is to provide a fatigue alarm apparatus and method, which have a short calculation time and will not make the driver lose alertness to the alarms. Further, the fatigue alarm apparatus and method have a simple product structure, and the driver should not wear a heavy equipment when driving.

To achieve at least the above objective, the present disclosure provides a fatigue alarm apparatus comprising a fatigue detector, a control unit and a stimulus alarm generator. The fatigue detector detects whether a driver is drowsy. The control unit is electrically connected to the fatigue detector and the stimulus alarm generator. When the fatigue detector detects that the driver is drowsy, the stimulus alarm generator controlled by the control unit to generate two stimulus alarms having a rest time period therebetween, and then, after an interval period elapses, the control unit determines whether an alarming procedure of generating the two stimulus alarms is to be interrupted or repeated, wherein the rest time period is less than the interval period.

In an embodiment of the present disclosure, the two stimulus alarms are two flashes having the rest time period therebetween.

In an embodiment of the present disclosure, the two stimulus alarms are "a flash with sound" and "sound" having the rest time period therebetween.

In an embodiment of the present disclosure, the rest time period matches a peak frequency of pre-stimulus alpha oscillations of the driver.

In an embodiment of the present disclosure, data of pre-stimulus alpha oscillations of the driver, which is measured in daily life of the driver, is obtained by the fatigue alarm apparatus, and the peak frequency of the pre-stimulus alpha oscillations of the driver is determined by the data of pre-stimulus alpha oscillations of the driver.

In an embodiment of the present disclosure, the rest time period is 75 to 92 microseconds.

In an embodiment of the present disclosure, the interval period is 1000 to 1700 microseconds.

In an embodiment of the present disclosure, the fatigue alarm apparatus executes the alarming procedures, and the rest time periods in the alarming procedures are different from each other.

In an embodiment of the present disclosure, the stimulus alarm generator is a light flashing unit.

In an embodiment of the present disclosure, the fatigue detector comprises an infrared camera, an assistant light source and an analyzing circuit. The infrared camera captures face images of the driver. The assistant light source provides an infrared luminance for the face. The analyzing circuit determines whether the driver is drowsy according to the images.

In an embodiment of the present disclosure, the fatigue alarm apparatus further comprises a power/mode switching unit and a status display unit. The power/mode switching unit electrically connected to the control unit is pressed by the driver to switch the alarming procedure to be a first and second alarming procedure. The status display unit electrically connected to the control unit displays status of the fatigue alarm apparatus.

In an embodiment of the present disclosure, the control unit comprises a counter for counting the rest time period and the interval period.

In an embodiment of the present disclosure, the alarming procedure is interrupted when a number of the alarming procedures executed reaches a specific number.

In an embodiment of the present disclosure, power of the fatigue alarm apparatus receives is supplied from the vehicle, such as the cigarette lighter receptacle.

In an embodiment of the present disclosure, the fatigue alarm apparatus is a smart phone in which a specific program is installed.

In an embodiment of the present disclosure, the light flashing unit is disposed on a top portion of a housing of the fatigue alarm apparatus, such that the flash generated by the light flashing unit is projected to ceiling of the vehicle for warning the driver and passengers.

In an embodiment of the present disclosure, the rest time period in the alarming procedure which is executed first time is initially 87.5 microseconds.

To achieve at least the above objective, the present disclosure provides a fatigue alarm method comprising: detecting whether a driver is drowsy to generate a fatigue detection result; generating, in response to the fatigue detection result, two stimulus alarms having a rest time period therebetween, and then elapsing an interval period, wherein the rest time period is less than the interval period; and determining whether an alarming procedure of generating the two stimulus alarms is to be interrupted or repeated.

To sum up, the provided fatigue alarm apparatus and method do not need a long calculation time, and can avoid the driver from losing alertness to the stimulus alarms. Moreover, the driver does not need to wear other measuring equipment.

BRIEF DESCRIPTION OF THE DRAWINGS

In order that the present disclosure may be better understood and readily carried into effect, certain embodiments of the present disclosure will now be described with reference to the accompanying drawings, wherein.

DETAILED DESCRIPTION OF THE PREFERRED EMBODIMENTS

Figure 1:
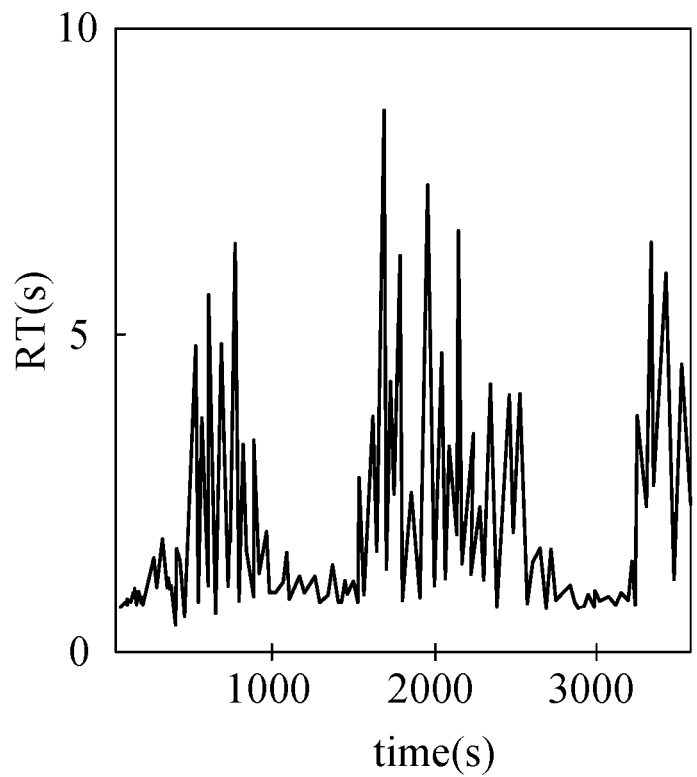
FIG. 1 is a diagram showing trial reaction times (RT) in one-hour session.

To make it easier for the examiner to understand the objects, characteristics and effects of this present disclosure, embodiments together with the attached drawings for the detailed description of the present disclosure are provided.

The present disclosure is to provide a fatigue alarm apparatus and method, which utilize two flash stimuli or two beep stimuli accompanied by a prior flash to ensure defensive driving by augmenting visual perception of the driver due to illusions. The illusion of pseudo flash or color fusion within the two stimuli is easy to generate just before drowsy driving occurs if phases of the two stimuli and pre-stimulus alpha oscillations match.

The pre-stimulus alpha oscillations are gradually excited in cerebral cortex and raised to a strong level before the driver falls asleep, therefore they are the one of most reliable signals to detect drowsy driving if the skin-contact electrodes and wires are available during every driving session. The present disclosure dispenses with electrodes but gives two flash stimuli or two beep stimuli accompanied by a prior flash to the driver. During defensive driving, the driver could correctly sense the two stimuli. But, just before drowsy driving occurs, the driver has a sensory illusion including a pseudo flash or a color fusion within the two stimuli. For example, the driver senses triple flashes under the two flash stimuli with the same color and sense a fusion color under the two flash stimuli with two different colors or complementary colors. The illusion is sensible only when phase of the two stimuli matches the phase of pre-stimulus alpha oscillations just before drowsy driving occurs. It means that the driver has the greatest possibility to sense the illusion when a rest time period between the two stimuli matches frequency of the pre-stimulus alpha oscillations just before drowsy driving occurs.

Annoyances, overloaded sensory and fail alarms are precluded during driving by using the fatigue alarm apparatus and method of the present invention. Because the alarm from pseudo flash or fusion color only appears just before drowsy driving occurs, the visible perception quickly raises for the perfect alarming time and correct warning. For further decreasing the number of flashes and increasing the visible perception, two beep stimuli accompanied by a prior flash are disclosed in an embodiment of the present disclosure. In the right situation and phase, drivers sense double flashes accompanied by double beeps instead of one flash accompanied by the beep first and another beep later. The impact of sensing double flashes is greater than the one of sensing triple flashes. Either double flashes or triple flashes dramatically raise the vision perception and successfully decrease the level of pre-stimulus alpha oscillations in cerebral cortex until the drivers get their clear conscious back.

Details and principles of embodiments of a fatigue alarm apparatus and method provided by the present disclosure are illustrated as follows. Before illustrating the fatigue alarm apparatus and method provided by the present disclosure, concepts of illusion which is generated by matching the rest time period and the peak frequency associated with the wave of the pre-stimulus alpha oscillations of the driver are described.

Figure 2:
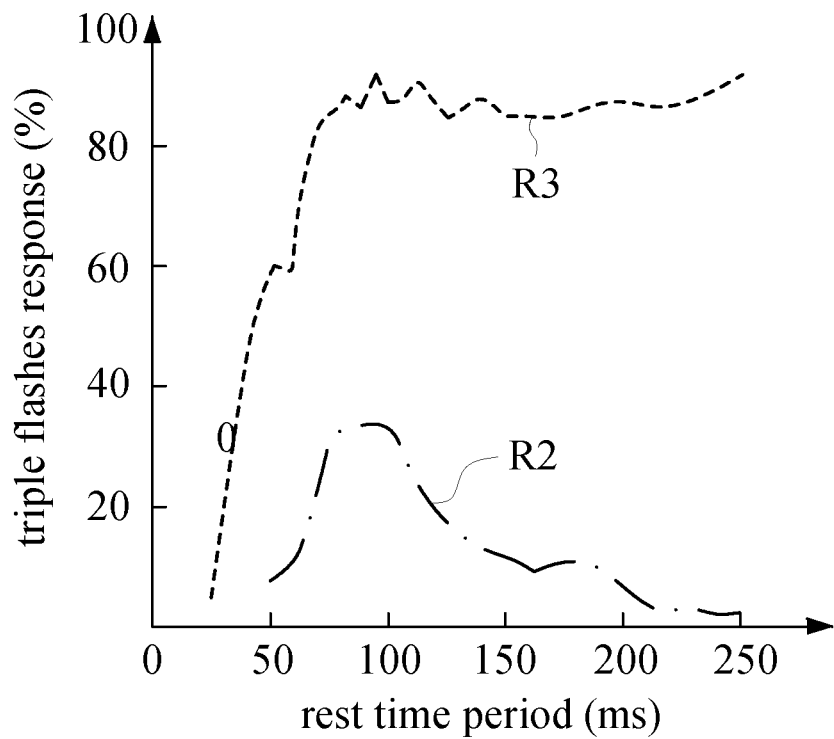
FIG. 2 is a curve diagram showing triple flashes response for three flash stimuli and two flash stimuli.

FIG. 1 and FIG. 2 are examples for the illusion of triple flashes. Participants were told to push the button for perception of triple flashes but not told that they were in trials of two flash stimuli or trials of three flash stimuli. Reaction times (RT) of the participants usually fluctuate like FIG. 1 in one-hour session. In study of electroencephalographic (EEG) correlates, events of 0.8 or greater seconds for RT strongly correlate to the dramatically raising mean-baseline-power of EGG (not shown). In trials of three flash stimuli (R3), triple flashes are sensed over 80% when rest time period within the flashes is greater 63 ms. For most of participants, 0.063 s are large enough to distinguish flashes. In trials of two flash stimuli (R2), illusion of triple flashes mostly happen in longer RT and in trials of the rest time period between 75 ms and 92 ms (FIG. 2).

The illusion of triple flashes results from alpha-band reverberation of visual perception. As we mentioned above, pre stimulus alpha oscillations in cerebral cortex are gradually excited before the driver falls asleep. The higher level of pre stimulus alpha oscillations result in the higher rate for illusion of triple flashes and the stronger alarm from visual perception.

The human being can have the illusion, while the frequency of the stimulus alarm is approximate to the peak frequency of the wave of the pre-stimulus alpha oscillations associated with the human brain (i.e. the rest time period between the two stimulus alarms matches the peak frequency of the wave of the pre-stimulus alpha oscillations associated with the human brain). For example, the peak frequency is 10 Hz (i.e. the period of the peak value is 100 microseconds), and when two flashes caused to the human being have a rest time period of 100 microsecond, the human being sees three flashes due to the illusion. For example, the peak frequency is 10 Hz, and when the "flash with sound" and the sound, to the human being, have the rest time period of 100 microsecond, the human being sees two flashes due to the illusion. The driver is taught to think about whether the illusion has happened, and the driver can keep high vision perception and awareness.

Figure 3:
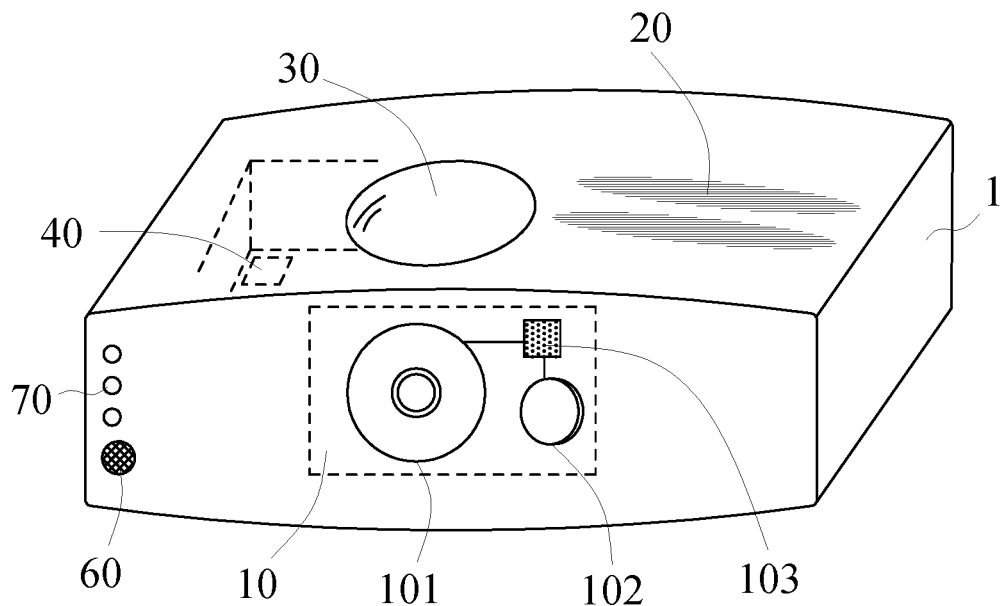
FIG. 3 is a schematic diagram showing a fatigue alarm apparatus according to an embodiment of the present disclosure.
Figure 4:
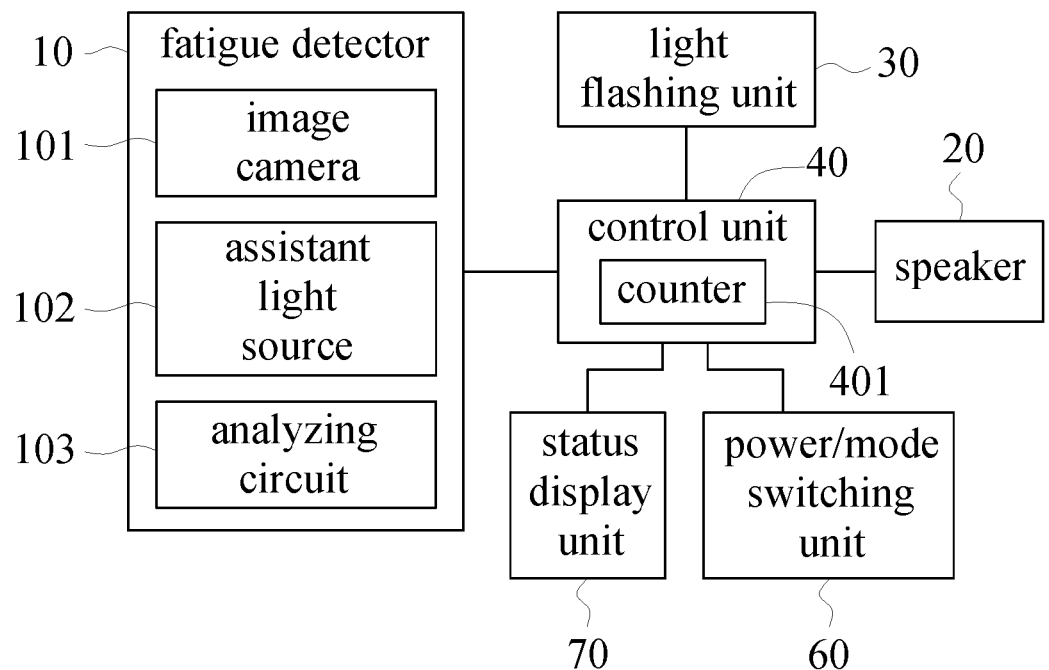
FIG. 4 is a block diagram showing the fatigue alarm apparatus of FIG. 3.

Referring to FIG. 3 and FIG. 4, FIG. 3 is a schematic diagram showing a fatigue alarm apparatus according to an embodiment of the present disclosure, and FIG. 4 is a block diagram showing the fatigue alarm apparatus of FIG. 3. The fatigue alarm apparatus 1 comprises a fatigue detector 10, a speaker 20, a light flashing unit 30, a control unit 40, a power/mode switching unit 60 and a status display unit 70. The control unit 40 is electrically connected to the fatigue detector 10, the speaker 20, the light flashing unit 30, the control unit 40, the power/mode switching unit 60 and the status display unit 70.

The fatigue detector 10 is used to detect whether a driver is drowsy. The fatigue detector 10 can detect whether a driver is drowsy according to IR images of driver's eyes, a measured breath amount and/or other parameter for evaluating fatigue, and the present disclosure is not limited thereto. In the embodiment, the fatigue detector 10 is disposed to capture an image of the face of the driver, and the captured image can be analyzed to detect whether the driver is drowsy. For example, partial components of the fatigue detector 10 are disposed at the front side of the fatigue alarm apparatus 1, but the present disclosure is not limited thereto.

In the embodiment, the fatigue detector 10 comprises an image camera 101, an assistant light source 102 and an analyzing circuit 103. The image camera is used to capture the image of the face of the driver, and can be an infrared camera. The assistant light source 102 emits IR light source to the face of the driver, so as to enhance the IR image. The analyzing circuit 103 is used to analyze the captured images to detect whether the driver is drowsy, for example, by analyzing an eyelids-closing level of the driver in the captured image. However, it is noted that, the analyzing manner of the analyzing circuit 103 is not used to limit the present disclosure.

The control unit 40 receives a fatigue detection result from the fatigue detector 10, and controls the light flashing unit 30 and the speaker 20 according to the fatigue detection result. The control unit 40 has a counter 401 for counting the rest time period and an interval period between two continuous alarming procedures. The light flashing unit 30 and the speaker 20 are controlled to flash and sound respectively. The light flashing unit 30 and the speaker 20 can be disposed on the top side of the fatigue alarm apparatus 1. Further, the light flashing unit 30 can be a wide-angle light source, and the present disclosure is not limited thereto.

In the embodiment, the alarming procedure can be determined by the input of the driver accompanied with the power/mode switching unit 60. When the power/mode switching unit 60 is pressed for a long time, for example, 10 seconds, the control unit 40 controls the fatigue alarm apparatus 1 to be turned on or off. When the power/mode switching unit 60 is pressed but not for the long time, the control unit 40 controls the fatigue alarm apparatus 1 to switch the alarming procedure to be a first or second alarming procedure. The power/mode switching unit 60 can be disposed at the front side of the fatigue alarm apparatus 1, but the present disclosure is not limited thereto.

The status display unit 70 is used to display the status of the fatigue alarm apparatus, for example, the status that the first or the second alarming procedure is selected. The status display unit 70 can be several light units disposed at the front side of the fatigue alarm apparatus 1, but the present disclosure is not limited thereto.

When the fatigue detection result shows the driver is drowsy, and the first alarming procedure is selected, the control unit 40 controls the light flashing unit 30 to flash, and after the rest time period counted by the counter 401 has reached, the control unit 40 controls the light flashing unit 30 to flash again. As mentioned above, if the driver is drowsy, the illusion that the driver sees three flashes can happen. Next, after the interval period counted by the counter 401 has reached, the control unit 40 determines whether the first alarming procedure is to be interrupted. If the first alarming procedure is not to be interrupted, the first alarming procedure (i.e. comprising the actions of flashing twice and counting the rest time period and the interval period) is executed again. Further, the interval period can be 1000 to 1700 microseconds, and the present disclosure is not limited thereto.

When the fatigue detection result shows the driver is drowsy, and the second alarming procedure is selected, the control unit 40 controls the light flashing unit 30 to flash and the speaker 20 to sound, and after the rest time period counted by the counter 401 has reached, the control unit 40 controls the speaker 20 to sound again. As mentioned above, if the driver is drowsy, the illusion that the driver sees two flashes can happen. Next, after the interval period counted by the counter 401 has reached, the control unit 40 determines whether the first alarming procedure is to be interrupted. If the first alarming procedure is not to be interrupted, the first alarming procedure (i.e. comprising the actions of flashing twice and counting the rest time period and the interval period) is executed again.

The determination manner for interrupting the first or second alarming procedure is to determine whether the number the first or second alarming procedures executed has reached a specific number (such as 5), the driver has pushed the power/mode switching unit 60, the fatigue detector 10 detects the driver is not drowsy, or the driver speaks he or she is not drowsy (i.e. the microphone can be included in the fatigue alarm apparatus 1). In short, the determination manner for interrupting the first alarming procedure is not used to limit the present disclosure.

As mentioned above, the rest time period is determined by the peak frequency of the wave of the pre-stimulus alpha oscillations of the driver. Therefore, the fatigue alarm apparatus 1 can receive the data of the pre-stimulus alpha oscillations of the driver, and the data of the pre-stimulus alpha oscillations of the driver is measured when the driver gets sleep in daily life, such that the fatigue alarm apparatus 1 can obtain the peak frequency of the wave of the pre-stimulus alpha oscillations of the driver.

In another embodiment, the rest time period is not determined by the peak frequency of the wave of the pre-stimulus alpha oscillations of the driver. The first or second alarming procedures are executed several times, and the rest time periods of the first or second alarming procedures are different. For example, the rest time periods are 75 to 92 microseconds in the first or second alarming procedures, and one rest time period may match the peak frequency of the wave of the pre-stimulus alpha oscillations of the driver. It is noted that, the rest time periods of the different drivers may have an average value, for example, 87.5 microseconds, and the rest time period can firstly be selected to the average value. Further, the profile of the driver, such as gender, age and race can be input to the fatigue alarm apparatus 1, and the rest time period can firstly be selected a specific value according the input profile of the driver.

Figure 5:
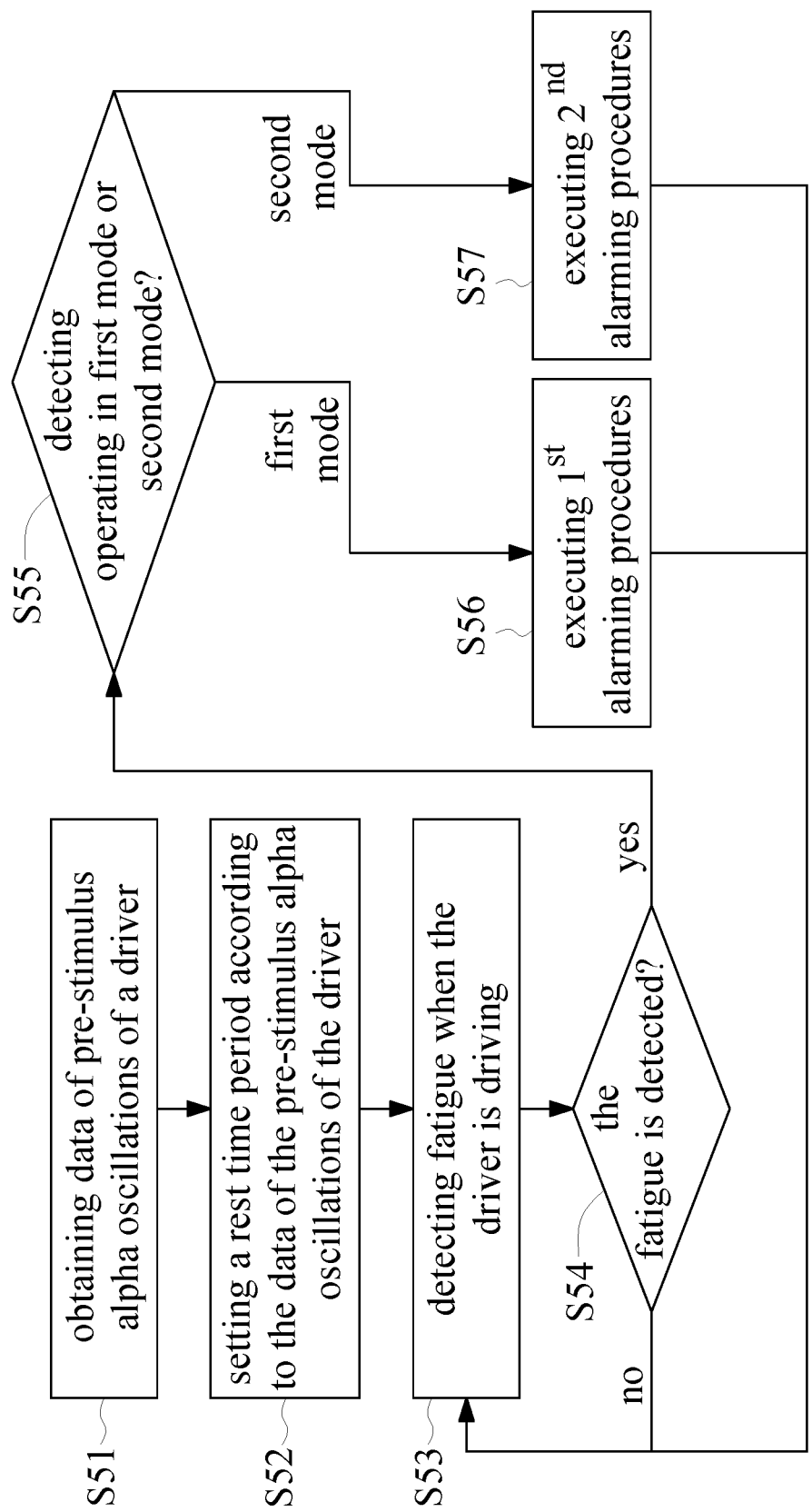
FIG. 5 is a flow chart showing a fatigue alarm method according to an embodiment of the present disclosure.

Next, referring to FIG. 5, FIG. 5 is a flow chart showing a fatigue alarm method according to an embodiment of the present disclosure. The fatigue alarm method comprises steps S51 to S57, and can be executed in the above fatigue alarm apparatus 1 or a smart phone (as described in FIG. 9). At step S51, data of pre-stimulus alpha oscillations of a driver is obtained. The data of the pre-stimulus alpha oscillations of the driver is used to determine the peak frequency of the pre-stimulus alpha oscillations of the driver, and can be measured when the driver gets sleep in daily life.

Then, at step S52, a rest time period is set or determined according to the data of the pre-stimulus alpha oscillations of the driver, and therefore the rest time period matches the peak frequency of the pre-stimulus alpha oscillations of the driver. Thus, the two stimulus alarms having the rest time period therebetween in one alarm procedure make the driver have illusion as mentioned above.

Next, at step S53, whether the driver is drowsy is detected. At step S54, whether the fatigue detection result shows the driver is drowsy is judged. If the driver is not drowsy, step S53 is executed again; otherwise, step S55 is executed. At step S55, whether the first or second mode (i.e. the first or second alarming procedure) is selected to be executed. If the first mode is selected, step S56 is executed; otherwise, step S57 is executed. At step S56, the first alarming procedures are executed, and at step S57, the second alarming procedures are executed.

Figure 6:
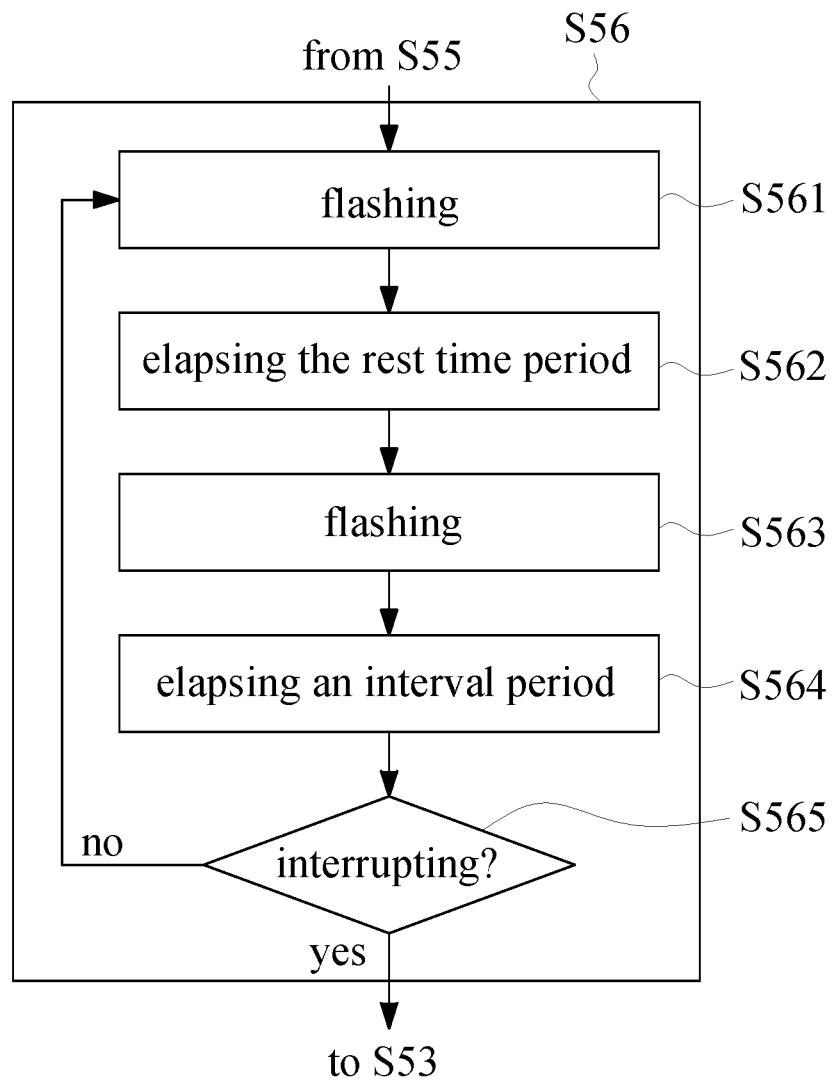
FIG. 6 is a flow chart showing a first alarming procedure of the fatigue alarm method of FIG. 5.

Next, referring to FIG. 6, FIG. 6 is a flow chart showing a first alarming procedure of the fatigue alarm method of FIG. 5. The step S56 comprises step S561 to S565. At step S561, a flash is generated. Next, at step S562, the rest time period elapses. Then, at step S563, another flash is generated. At step S564, the interval period elapses. At step S565, whether the first alarming procedure is to be interrupted, for example, whether the number of the first alarming procedures executed reaches a specific number, is determined. If the first alarming procedure is to be interrupted, step S53 is executed; otherwise, step S561 is executed.

Figure 7:
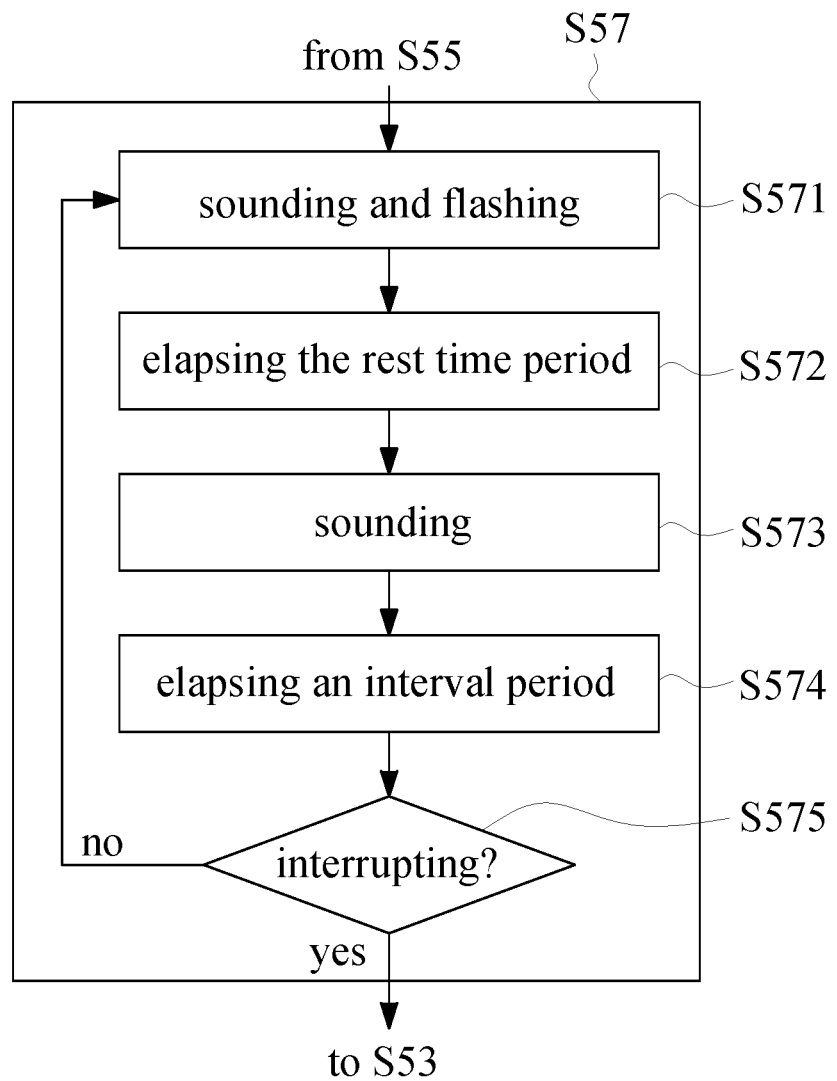
FIG. 7 is a flow chart showing a second alarming procedure of the fatigue alarm method of FIG. 5.

Next, referring to FIG. 7, FIG. 7 is a flow chart showing a second alarming procedure of the fatigue alarm method of FIG. 5. The step S57 comprises step S571 to S575. At step S571, a flash and sound are generated. Next, at step S572, the rest time period elapses. Then, at step S563, another sound is generated. At step S574, the interval period elapses. At step S575, whether the second alarming procedure is to be interrupted, for example, whether the number of the second alarming procedures executed reaches a specific number, is determined. If the second alarming procedure is to be interrupted, step S53 is executed; otherwise, step S571 is executed.

Figure 8:
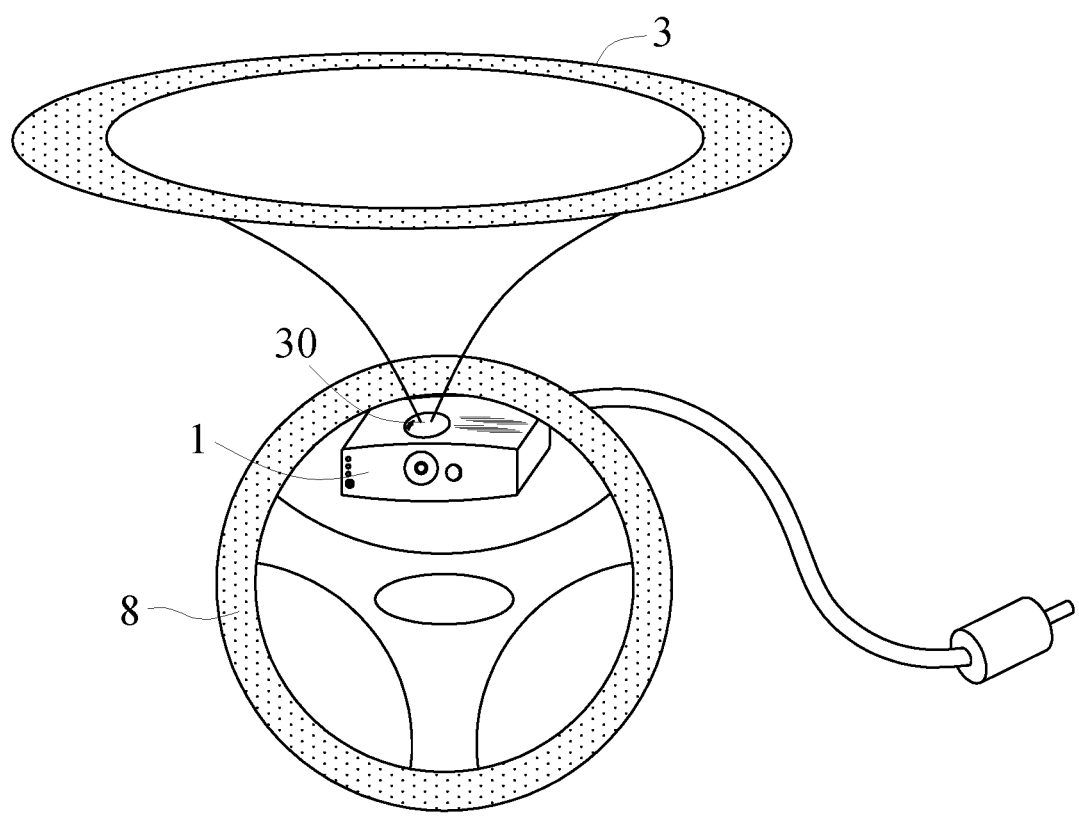
FIG. 8 is a schematic diagram showing usage of the fatigue alarm apparatus of FIG. 3.

Next, referring to FIG. 8, FIG. 8 is a schematic diagram showing usage of the fatigue alarm apparatus of FIG. 3. The fatigue alarm apparatus 1 of FIG. 3 can be placed in front of the steering wheel 8, and the flash 3 generated from the light flashing unit 30 of the fatigue alarm apparatus 1 is projected on top of the driver and the passenger. The power of the fatigue alarm apparatus 1 can be supplied by the car battery through the cigarette lighter receptacle.

Figure 9:
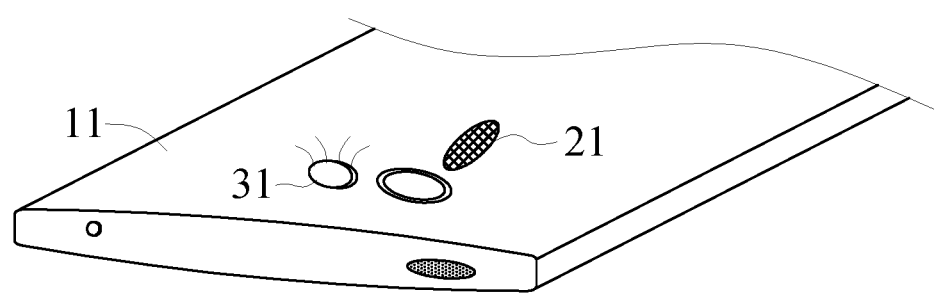
FIG. 9 is a schematic diagram showing usage of the fatigue alarm method of FIG. 5.

Next, referring to FIG. 9, FIG. 9 is a schematic diagram showing usage of the fatigue alarm method of FIG. 5. A smart phone 11 comprising a light flashing unit 31 and a speaker 21 can be used to execute the fatigue alarm method of FIG. 5. The program of the fatigue alarm method is installed in the smart phone 11, such that the processor of the smart phone 11 can utilize the components of the smart phone 11 to detect whether the driver is drowsy, and control the speaker 21 and the light flashing unit 31 to sound and flash when that the driver is drowsy is detected.

In conclusion, the provided fatigue alarm apparatus and method in the embodiment of the present disclosure utilize the illusion effect generated by matching the rest time period between the two stimulus alarms and the peak frequency of the pre-stimulus alpha oscillations of the driver, to make the driver conscious by augmenting visual perception of the driver due to illusions. Therefore, the provided fatigue alarm apparatus and method do not need a long calculation time, and can avoid the driver from losing alertness to the stimulus alarms. Moreover, the driver does not need to wear other measuring equipment.

While the present disclosure has been described by means of specific embodiments, numerous modifications and variations could be made thereto by those skilled in the art without departing from the scope and spirit of the present disclosure set forth in the claims.

What is claimed is:

1. A fatigue alarm apparatus, comprising:
   a fatigue detector, detecting whether a driver is drowsy; and
   a control unit, electrically connected to the fatigue detector; and
   a stimulus alarm generator, electrically connected to the detector;
   wherein, when the fatigue detector detects that the driver is drowsy, the stimulus alarm generator controlled by the control unit generates two stimulus alarms having a rest time period therebetween, and then, after an interval period elapses, the control unit determines whether an alarming procedure of generating the two stimulus alarms is to be interrupted or repeated, wherein the rest time period is less than the interval period;
   wherein the rest time period matches a peak frequency of pre-stimulus alpha oscillations of the driver.

2. The fatigue alarm apparatus according to claim 1, wherein data of pre-stimulus alpha oscillations of the driver, which is measured in daily life of the driver, is obtained by the fatigue alarm apparatus, and the peak frequency of the pre-stimulus alpha oscillations of the driver is determined by the data of pre-stimulus alpha oscillations of the driver.

3. The fatigue alarm apparatus according to claim 1, wherein the alarming procedure is interrupted when a number of the alarming procedures executed reaches a specific number.

4. The fatigue alarm apparatus according to claim 1, wherein the stimulus alarm generator comprising a light flashing unit is disposed on a top portion of a housing of the fatigue alarm apparatus, such that a flash generated by the light flashing unit is projected to ceiling of a vehicle for warning the driver and passengers.

5. The fatigue alarm apparatus according to claim 1, wherein the stimulus alarm generator comprising a light flashing unit and a speaker is disposed on a top portion of a housing of the fatigue alarm apparatus, such that a flash generated by the light flashing unit is projected to ceiling of a vehicle for warning the driver and passengers.

6. A fatigue alarm method, comprising:
   detecting whether a driver is drowsy to generate a fatigue detection result;

generating, in response to the fatigue detection result, two stimulus alarms having a rest time period therebetween, and then elapsing an interval period, wherein the rest time period is less than the interval period; and
determining whether an alarming procedure of generating the two stimulus alarms is to be interrupted or repeated;
wherein the rest time period matches a peak frequency of pre-stimulus alpha oscillations of the driver.

\* \* \* \* \*